United States Patent [19]

Mannion et al.

[11] Patent Number: 5,195,518
[45] Date of Patent: Mar. 23, 1993

[54] SYSTEM AND METHOD FOR ENHANCING COLLATERAL CARDIAC BLOOD FLOW

[75] Inventors: John D. Mannion, Mount Laurel, N.J.; Michael G. Magno, Oxford, Pa.

[73] Assignee: Thomas Jefferson University, Philadelphia, Pa.

[21] Appl. No.: 756,157

[22] Filed: Sep. 6, 1991

[51] Int. Cl.$^5$ .............................................. A61F 2/16
[52] U.S. Cl. ................................. 128/421; 128/419 P; 600/16; 600/17
[58] Field of Search .................... 600/16, 17; 623/3; 128/419 PG, 419 P, 421

[56] References Cited

U.S. PATENT DOCUMENTS

| | | | |
|---|---|---|---|
| 4,944,299 | 7/1990 | Silvian | 128/419 PG |
| 4,979,936 | 12/1990 | Stephenson et al. | 600/16 |
| 5,007,927 | 4/1991 | Badylak et al. | 600/16 |
| 5,067,960 | 11/1991 | Grandjean | 600/16 |

OTHER PUBLICATIONS

Mannion, J. D. et al., "Hydraulic Pouches of Canine Latissimus Dorsi-Potential For Left Ventricular Assistance," 91(4), *J. Thoracic & Cardiovas. Surg.* 534 (Apr. 1986).

Mannion, J. D. et al., "Potential Uses of Skeletal Muscle For Myocardial Assistance," *Surgical Clinics of North America*, vol. 65, No. 3, Jun. 1985.

*Primary Examiner*—Kyle L. Howell
*Assistant Examiner*—George Manuel
*Attorney, Agent, or Firm*—Woodcock Washburn Kurtz Mackiewicz & Norris

[57] ABSTRACT

There is provided a system and method for enhancing collateral blood flow to the heart of a patient having angina with otherwise normal cardiac function. Skeletal muscle from the patient is attachd to the left ventricle, and stimulated with both chronic and acute stimulation to provide chronic long-term collateral blood flow and increased acute collateral blood flow during periods of exercise or times when angina is at greater risk. The stimulation system includes a sensor for determining cardiac demand and/or for sensing natural heartbeats, and processing circuitry for acutely increasing stimulation of the skeletal muscle in response to the sensor or natural rate. The system is further provided with internal clock means for causing cessation of delivery of stimulus pulses during periods of low activity, and external programming means for programming changes in either chronic or acute stimulation.

12 Claims, 2 Drawing Sheets

SYSTEM AND METHOD FOR ENHANCING COLLATERAL CARDIAC BLOOD FLOW

This invention was made in the course of research supported by a grant from the National Institutes of Health. The government may have certain rights in this invention.

BACKGROUND OF THE INVENTION

1. Field of the Invention

This invention lies in the field of cardiac assist procedures and, more specifically, to a system and method for enhancing the use of skeletal muscle in providing collateral blood flow to risk regions of the heart such as chronic ischemic myocardium.

2. Description of the Prior Art

There currently exists a class of cardiac patients who manifest angina, but for whom conventional medical therapy is not indicated, and who are not candidates for more severe procedures such as implantation of cardiac assist devices. Direct revascularization of ischemic mycardium with a coronary bypass to a large epicardial vessel is not always possible because of extensive distal coronary artery disease. Despite improvements in medical management, it has been found that about 5% of patients are considered inoperable, i.e., cannot undergo revascularization with angioplasty or surgery, because of distal disease. In addition, other patients who presently do undergo such palliative revascularization might be better served by a more effective indirect revascularization procedure.

Cardiomyoplasty, which involves wrapping the latissimus dorsi muscle around the left ventricle and stimulating the skeletal muscle to contract, is presently undergoing clinical trials in the United States under the guidance of the FDA. The mechanism of the augmentation of the cardiac function after cardiomyoplasty is thought to be primarily mechanical, resulting from a pincer-like compression of the left ventricle by the skeletal muscle. The skeletal muscle is stimulated by a cardiomyostimulator which delivers a series or burst of pulses to the skeletal muscle to evoke each contraction. It has also been known to use skeletal muscle to actually replace part of the heart or the aorta. Further, the skeletal muscle has been used to form a hydraulic pouch for cardiac assist, rather than to directly connect the muscle to the heart or the aorta. See Mannion, J. D. et al., "Hydraulic Pouches of Canine Latissimus Dorsi-Potential For Left Ventricular Assistance," 91(4) *J. Thoracic & Cardiovasc. Surg.* 534 (April 1986); U.S. Pat. No. 4,979,936, Stevenson et al., which is incorporated herein by reference. See also Mannion, J. D. et al., "Potential Uses of Skeletal Muscle For Myocradial Assistance," *Surgical Clinics of North America,* Vol. 65, No. 3, June 1985, which discusses several clinical applications for skeletal muscle in cardiac surgery.

However, in these procedures, the purpose is to provide mechanical assist, rather than supplying the myocardial tissue with sufficient blood to treat the angina. By contrast, the approach of this invention is to treat the angina by enhancing indirect revascularization of chronic ischemic mycardium.

Indirect revascularization of ischemic myocardium was an extensively studied topic before the advent of coronary artery bypass surgery. Eck and O'Shaunessey, among others, documented that myocardium could be supplied by extramyocardial collateral blood flow. However, the clinical usefulness of the concept of myocardial revascularization at the capillary level was never fully confirmed. While investigations did suggest that small amounts of blood from extramyocardial collaterals could perfuse myocardium, the total amount of extramyocardial blood flow was understood to be small. Because of the dramatic success of bypass surgery, research in indirect revascularization waned.

More recent observations in the area of coronary collateral circulation have stressed the importance of collaterals. In acute myocardial ischemia, myocardial collaterals have been implicated in improving regional myocardial function and survival rates after myocardial infarction, and in extending the time frame in which to perform successful reprofusion. The clinical evidence suggests that intracoronary collaterals, which are anatomically located in the endocardium, have an important functional role in many patients. Establishment of an additional extramyocardial source of collateral blood flow is anticipated to be helpful in relieving myocardial ischemia. However, as found by early investigators, the quantity of collateral blood flow from skeletal muscle is normally small.

Applicant's Background Studies

The applicant has performed several experiments concerning the development of collateral blood flow from skeletal muscle to myocardium in an animal model. First, applicant has demonstrated that nutrient collateral blood flow from skeletal muscle forms to normal capric myocardium. An extramyocardial collateral blood flow has been demonstrated in the past in other models; applicant, however, has measured the collateral blood flow with microspheres, and has found that the amount of the collateral blood flow from skeletal muscle to normal myo..ardium is small. Suspecting that one reason for the small quantity of collateral flow from skeletal muscle to normal myocardium is that there is an insufficient stimulus for collateral development, the applicant performed cardiomyoplasty in a model which includes normal, infarcted, and chronically ischemic myocardium. Skeletal muscle derived collateral flow to normal myocardium or infarct was negligible, but flows to chronic ischemic myocardium approached about 10% of the total flow to the chronic ischemic myocardium.

Applicant has now studied the effect of acute electrical stimulation o the skeletal muscle on collateral blood flow. In a model of chronic myocardial ischemia, in which a cardiomyoplasty had been performed, the skeletal muscle was stimulated at a 2 Hz frequency, and blood flow was measured. The blood flow to chronic ischemic myocardium which was derived from the skeletal muscle rose to about 50% of total flow to the chronically ischemic myocardium. The absolute blood flow to the ischemic myocardium—the combined intramyocardial and extramyocardial flow—did not increase, but the proportion arising from the skeletal muscle rose dramatically. The lack of a rise in the total myocardial blood flow in this model is explained by the fact that the myocardial oxygen demands were not elevated by the muscle stimulation. The only way to increase total myocardial blood flow is to lower myocardial capillary resistance with drug or exercise-induced vasodilation.

Applicant's studies have demonstrated that collateral blood flow to myocardium can be regulated with skeletal muscle stimulation. The level of muscle blood flow will determine the magnitude of collateral blood flow from skeletal muscle to chronic ischemic myocardium. Patients with viable, but chronically ischemic myocardium have the potential to form significant epicardial extramyocardial collaterals, which would complement the endocardial intramyocardial collateral system. There is thus a need for a system and method for enhancing such indirect myocardial revascularization, including use of a stimulation pattern to maximize both chronic and acute (short-term) muscle blood flow.

SUMMARY OF THE INVENTION

It is an object of this invention to provide a system and method for sustaining enhanced levels of skeletal muscle derived coronary collateral flow in patients where operative procedures are inapplicable because of distal vessel disease.

It is another object of this invention to provide a treatment for providing coronary collateral flow to patients who cannot benefit from direct myocardial revascularization because of extensive distal vessel disease, with treatment provides an optimization of chronic continuous stimulation of the skeletal muscle as well as enhancement of flow reserve by acute electrical stimulation of the skeletal muscle.

It is further more generalized object of this invention to provide a method of treatment and system for treatment of patients with ischemic cardiomyopathy, whereby skeletal muscle is effectively attached to the patient's left ventricle and stimulated both chronically and acutely in a manner which optimizes enhancement of collateral blood flow through the skeletal muscle to the cardiac muscle.

In accordance with the above objects, there is provided a system and method for providing collateral blood flow to the heart of a patient having angina with otherwise normal cardiac function. Skeletal muscle from the patient is attached to the patient's left ventricle and chronically stimulated in a manner that enhances long-term collateral blood flow to the patient's heart, and specifically to risk areas of chronic ischemia. The skeletal muscle is preferably sutured to the pericardium, whereby it engages the myocardium sufficiently for development of extramyocardial collaterals but without significant mechanical cardiac assist. Patient cardiac demand is monitored with a rate responsive pacemaker-type circuit, and the normal chronic stimulation of the skeletal muscle is modulated acutely to provide increased stimulation during times of greater patient exercise or cardiac demand. The stimulation output is also programmable by the patient for quick response angina treatment, and can be turned off automatically or manually during nighttime or other periods of low level activity. The treatment of the invention results in both formation of shunt collateral paths from normal heart muscle to areas of chronic ischemia, as well as extramyocardial collateral paths from the blood source associated with the skeletal muscle.

DESCRIPTION OF THE PREFERRED EMBODIMENT

Figure 1:
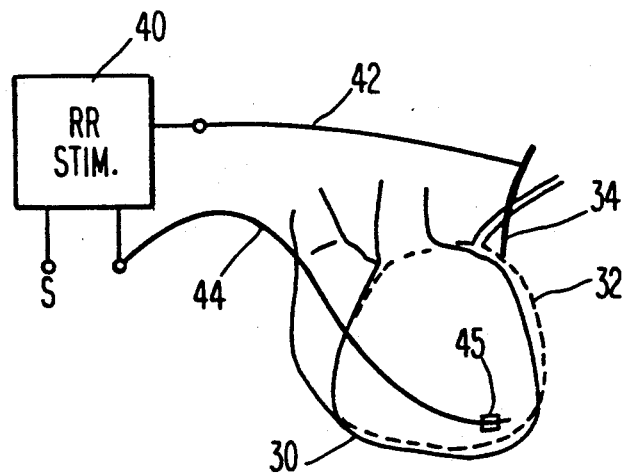
FIG. 1 is a schematic diagram showing the positioning of the skeletal muscle on the left ventricle, and the connections of the rate responsive cardiomyostimulator.

The preferred embodiment of this invention is to provide enhanced blood flow to risk areas of a patient's heart, e.g., myocardial areas of chronic ischemia. Toward this end, and as illustrated in FIG. 1, a portion of skeletal muscle 32 is operatively connected to the left ventricle 30 of the patient's heart. Preferably, a latissimus dorsi cardiomyoplasty is performed, with the pedicle sutured to the inside of the pericardium. The thoracodorsal nerve of the muscle will be dissected out, as illustrated schematically at 34, so that a pacing or stimulating electrode can be attached thereto. A cardiomyostimulator 40, such as one made by Medtronic, Inc., is implanted in the patient, and a lead 42 is connected from the stimulator to the motor nerve 34, for delivery of stimulus pulses thereto. The stimulator has a lead 44 attached thereto, with an electrode 45 implanted in the left ventricle, for sensing QRS signals, whereby the stimulus output can be synchronized with the patient's heartbeat, if desired. Also, the stimulator may be adapted to be rate responsive, in a manner that is well known in the cardiac pacing art. Rate responsive pacemakers operate by sensing a variety of rate-indicating parameters, including measurement of activity, blood temperature, blood oxygen, respiration, Q-T interval, and the like. A separate sensor S may be employed as illustrated, or in the case of the Q-T-type pacemaker the rate indicating signal is detected as a component of the heartbeat, by the lead 44.

By attachment of the skeletal muscle 32 to the pericardial sack (not shown), the skeletal muscle is permitted to perform adhesions to the epicardial heart wall. These adhesions permit the desired collateral blood flow, whether or not stimulation of the skeletal muscle causes any contractions which compress the left ventricle. By placing the skeletal muscle over a large portion or substantially all of the left ventricle, there is provided an opportunity for collateral formation of capillaries so as to shunt blood from normal heart tissue to chronic ischemic myocardium. Moreover, there is provided a new blood source through the muscle 32 to the area of chronic ischemic myocardium. Thus, it is clearly preferred to have the skeletal muscle cover over and adhere to normal heart muscle as well as the risk area, but it is not desired to wrap the muscle around in such a way as to ensure mechanical compression of the heart.

An important feature of the invention is the type of stimulation used to enhance collateral blood flow through the skeletal muscle. It is known that skeletal muscle is capable of changing its physiological, biochemical and structural logistics in response to exercise and electrical stimulation. When the skeletal muscle is electrically stimulated by its motor nerve, the entire muscle undergoes transformation so as to change its contraction characteristics. However, and more importantly to this invention, my studies have shown that stimulation of the skeletal muscle can provide chronic enhancement of the formation of collaterals to the normal myocardium. Of primary importance in this invention is the combination of both long-term stimulation for chronic enhancement of blood flow through the skeletal muscle, and short term stimulation for acute enhancement in order to deal with episodes of increased activity which might otherwise cause angina pain. However, chronic stimulation should be not be undertaken solely at a strength or intensity so as to maximize chronic blood flow, since this may condition the skeletal muscle to be resistant to short term responses of increased levels of stimulation aimed to increase levels of blood flow during the periods of greater exercise. For these reasons, the invention embraces chronic stimulation at a range of rate of energy levels, combined with periods of rest during which the skeletal muscle is not stimulated, so as to optimally condition the heart for both chronic and acute response. Thus, the chronic stimulation may be at a lower intensity than that which maximizes chronic collateral blood flow, in order to enable a better acute response. By sensing body demand for increased output from the heart through a rate responsive cardiomyostimulator, the system and method of the invention provide a short time response reaction to the patient's need for greater blood flow.

Figure 2:
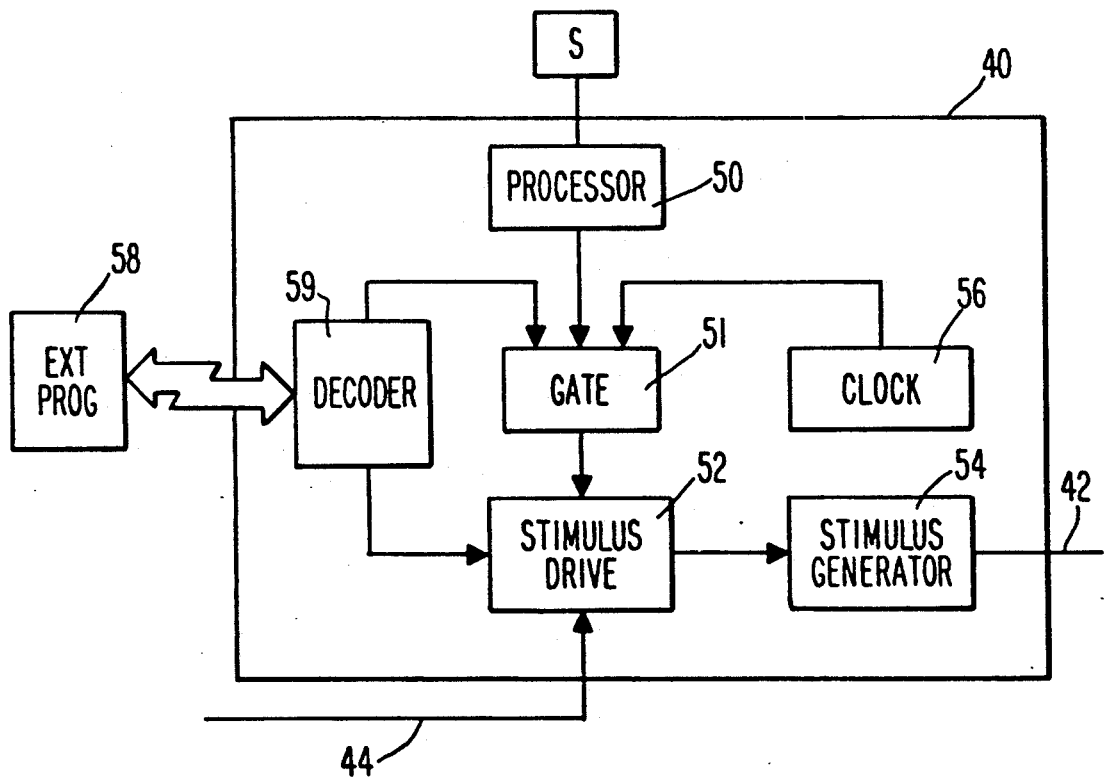
FIG. 2 is a block diagram of the improved cardiomyostimulator for use in the practice of this invention.

Referring now to FIG. 2, there is shown a block diagram of the primary components of the cardiomyostimulator 40 in accordance with this invention. A sensor S is connected electrically to a processor circuit 50, which converts the sensed transducer signal to an electronic signal reflective of desired heart rate or heart demand, in accordance with circuits and software well known in rate responsive pacemakers. The output of processor 50 is connected through a gate 51 to a stimulus drive circuit 52, which control output pulses of a frequency and size responsive to the information derived from the sensor S. The output of stimulus drive circuit 52 is connected to stimulus generator 54, which generates stimulus pulses in accordance with the stimulus drive output, and delivers them to the skeletal muscle motor nerve 34, or directly to the skeletal muscle, via lead 42. When the sensor S calls for more system blood flow, processor 50 delivers a signal to stimulus drive 52, which causes an output which is either increased in rate, or increased in the number or size of output signals for each burst. Thus, for example, under normal circumstances when the patient is moderately at rest, pulse generator may be controlled to output bursts of two pulses of a given energy level, synchronized to every other patient heartbeat, or, e.g., every fourth heartbeat. Processor 50 may be designed so that when a signal from sensor S exceeds a predetermined threshold, stimulus drive 52 causes three pulses to be generated each burst, i.e., bursts are generated at the same rate but an extra pulse is generated each burst. Alternately, stimulus drive 52 may be designed to increase stimulus level by increasing the rate of delivery of bursts, or increasing the stimulation by a combination of rate and number of pulses per burst. Still further, drive 52 can increase the time (width) and/or amplitude of each pulse in the burst in accordance with the signal from processor 50, so that the energy delivered from pulse generator 54 varies as the demand represented by the signal from sensor S. It is to be noted that many variations of stimulus response to sensor information are possible within the scope of the invention. Also, it is noted that where the heart responds naturally to provide an increased rate at times of increased exercise, the sensor may be bypassed, in which case heartbeat signals from lead 44 directly trigger the stimulus drive to output a burst of pulses each received heart signal, whereby increased stimulation automatically follows from increased natural heart rate. Further, the stimulation may be programmed to increase the rate of delivery of bursts as a function of sensed natural rate.

In another feature of the system and method of this invention, steps are taken to stop or decrease stimulation periodically, so as to further optimize the effective chronic stimulation and the concurrent ability of the skeletal muscle to respond to acute stimulation. Thus, a clock 56 is used to indicate a predetermined amount of time each night, e.g., 8 hours, at which time the patient is expected to be asleep, or at least not exercising. The clock output is connected to gate 51 so as to open it, so that stimulus drive 52 does not enable the pulse generator during the nighttime period. Since the patient is unlikely to experience angina while sleeping, stimulation and increased blood flow are not as important during this period, and the overall usefulness of the cardiomyoplasty may be enhanced by shutting off stimulation every night. In a similar manner, when processor 50 detects a level of activity below a predetermined threshold, stimulus drive 52 can be disabled.

In another embodiment, an external programmer 58, operable by the patient, can be used to initiate an increased or decreased stimulus output. External programmers are well known in the pacing art, and range from a simple magnet placed over the stimulator to a more complex programmer. By use of an external programmer 58, the patient can send a simple signal received and decoded at 59, and delivered through gate 51 to the stimulus drive 52, for increasing or decreasing the stimulation output of the device. Suitably, the decoder 59 includes a timer circuit, which can time out a predetermined period, such as 30 minutes, during which the decoder output holds the stimulus drive 52 in a condition for causing increased output from pulse generator 54. By limiting the time period for increased stimulation, the danger is reduced that the patient would maintain in a condition of increased stimulation over a period of time longer than that which is otherwise desirable.

Figure 3:
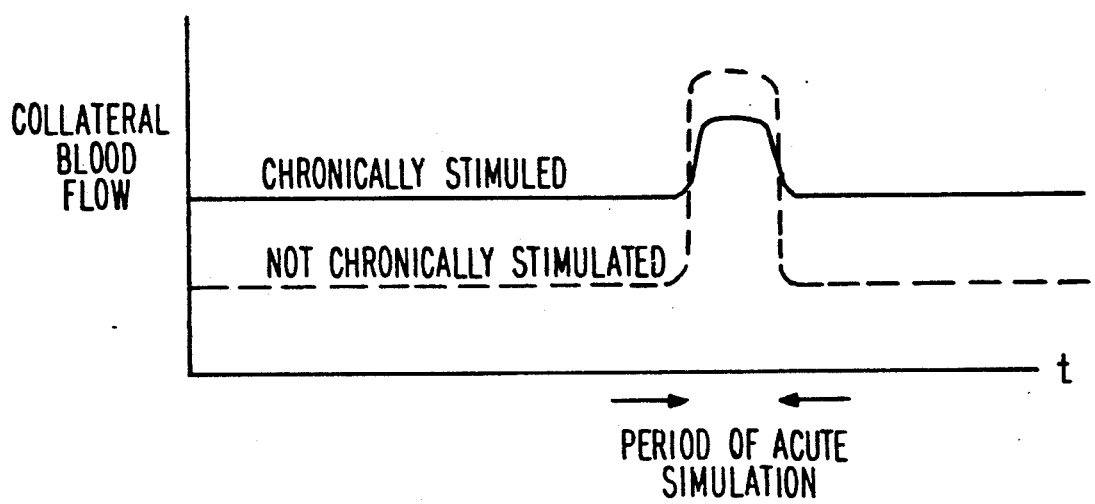
FIG. 3 is a chart illustrating ideal collateral blood flow response to chronic and acute stimulation of the skeletal muscle, in accordance with this invention.

Referring to FIG. 3, there is shown an idealized graph comparing blood flow through the skeletal muscle to the stimulus level applied to the skeletal muscle. For this figure, it is to be understood that during the period of acute stimulation, there is a step increase in the stimulation level of the muscle. For a given patient, a given basal stimulus level will produce a given collateral blood flow, e.g., about 10% of the normal cardiac capillary blood flow. Raising or lowering the basal stimulus level will produce, in most specimens of skeletal muscle, some change in basal collateral blood flow, but this response in most cases will not be anywhere near linear. As a general proposition, an increased chronic stimulus level will yield a somewhat higher blood flow, but a saturation point will be reached. Thus, blood flow cannot be increased to 100% chronic load, but only about 50%. Further, by stimulating chronically at a level below that of the saturation level, a greater transient, or acute response can be obtained due to short-term or acute increases in stimulation. As seen in the graph, a step increase in stimulus level results in a somewhat delayed increase in collateral blood flow. In the practice of this invention, the chronic stimulus level is maintained below that which would maximize chronic collateral blood flow, so as to optimize the combination of chronic collateral blood flow and flow reserve.

Figure 4A:
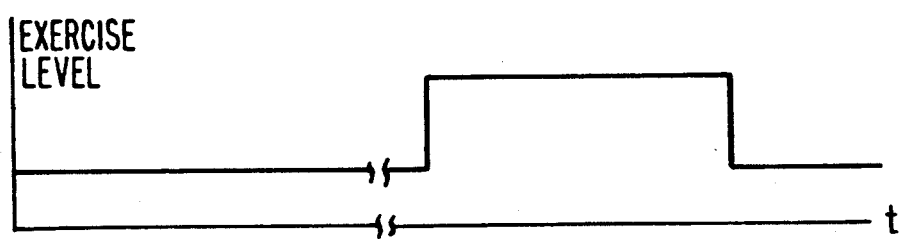
FIGS. 4A, 4B and 4C illustrate stimulator output in time relation to patient heartbeat and patient exercise level.
Figure 4B:
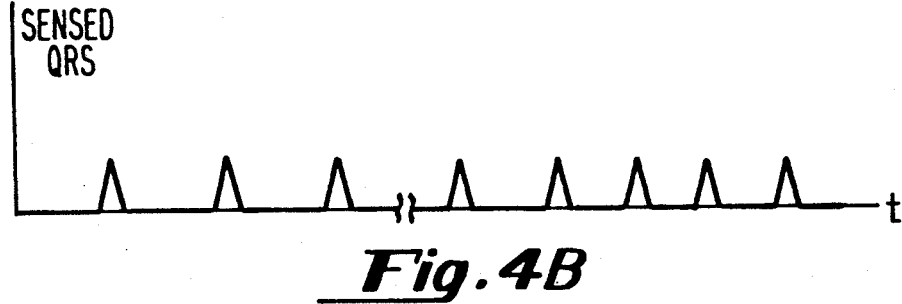
Figure 4C:
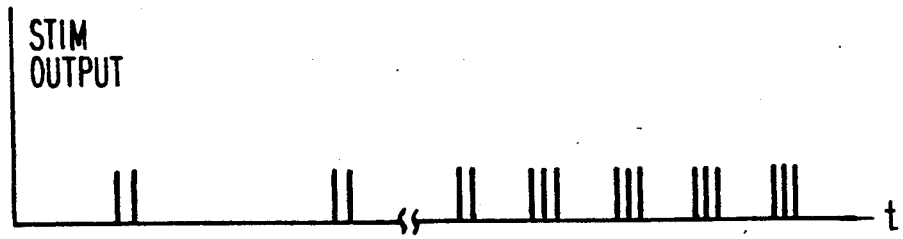

Referring to FIGS. 4A, B and C, there is shown an idealized step change in exercise level, patient heartbeat (QRS), and stimulator output respectively. For basal exercise level as indicated in 4A, there is illustrated a corresponding relatively constant heartbeat at a nominal rate. Corresponding to the basal exercise level, there is maintained a chronic stimulus output, constituting bursts of two pulses each, delivered synchronously every other heartbeat. It is to be emphasized that this relationship is illustrative only, and the invention is in no way limited to this illustration. Thus, for example, the bursts need not be synchronized, although this is preferable for reasons discussed below. During the step increase of exercise level, it is seen that the heartbeat responds by assuming a higher rate. As illustrated, the heartbeat does not immediately jump up to a higher rate, but responds by increasing rate with some time delay. However, for illustrative purposes, there is shown a step increase in heartbeat, and a corresponding increase in the rate of delivering stimulus output bursts. As illustrated in FIG. 4C, the pacer output is illustrated as being changed in two ways during the period of exercise: the bursts occur at a greater rate, and each burst contains three pulses instead of two. Of course, again it is to be understood that this is illustrative only, and the response by which increased acute stimulus is provided can be varied in any manner in accordance with this invention.

Other variations of the disclosed system and method of treatment are within the scope of the invention. Thus, the correlation between the sensed rate signal and change in stimulus can be programmed through programmer 58, in accordance with techniques well known in the cardiac pacing art. In terms of surgical procedure, local growth factors may be used to enhance angiogenesis between skeletal muscle and myocardium. Heparin, and acidic and basophilic growth factors can be used for this purpose.

It is to be noted that when the skeletal muscle is stimulated, it will contract to some degree, although this is not the primary intended effect. Since the skeletal muscle will contract, it should be stimulated to do so in synchrony with the heart's contractions. This synchrony will prevent the heart's filling in diastole, and provide some degree of mechanical assist. Note that contraction of the skeletal muscle synchronously with the heart provides that diastole likewise is synchronous, so that blood flow can leave the skeletal muscle during diastole. The primary purpose of the stimulation, however, is to stimulate blood flow to the skeletal muscle, and from there to the heart.

It is further noted that the stimulator system of this invention may also comprise a conventional rate responsive pacemaker for pacing the heart, as well as stimulating the skeletal muscle. The stimulator system of this invention embraces such a combined system, and further embraces any hardware or software means for increasing the stimulation level to the skeletal muscle at times of acute need for greater cardiac output.

What is claimed:

1. A method of providing collateral blood flow through a patient's skeletal muscle to a patient's myocardial tissue, comprising:

a) operatively connecting a skeletal muscle pedicle of the patient to said myocardial tissue, the muscle pedicle retaining its source of blood flow;

b) attaching a stimulator to said skeletal muscle and delivering stimulus pulses from said stimulator to said skeletal muscle; and c) controlling said stimulator to deliver chronic stimulus pulses to said muscle in accordance with a chronic pattern so as to provide chronic collateral blood flow from said muscle to said myocardium, and changing the pattern of delivering stimulus pulses for acute periods during increased levels of patient cardiac demand, said controlling providing for increased collateral flow from said skeletal muscle to said myocardial tissue.

2. The method as described in claim 1, comprising sensing a body parameter reflective of cardiac demand, and controlling said acute stimulation in response to said sensed parameter.

3. The method as described in claim 1, wherein said attaching step is performed by suturing said pedicle to the patient's pericardium.

4. The method as described in claim 1, wherein the step of chronically stimulating comprises delivering stimulus pulses to said skeletal muscle at a rate less than the patient's heart rate.

5. The method as described in claim 4, wherein said chronic stimulation pulses are delivered substantially synchronously with patient heartbeats.

6. The method as described in claim 5, wherein said changing comprises delivering stimulus pulses which are at a multiple of said chronic rate.

7. The method as described in claim 1, wherein said changed pattern for acute periods comprises increasing the energy delivered to the skeletal muscle with each stimulus pulse.

8. The method as described in claim 1, further comprising the step of periodically automatically determining a rest period, and inhibiting delivery of chronic stimulation pulses during said rest period.

9. The method as described in claim 1, comprising delivering a control signal from external to said patient to enable an acute increase in stimulation of said skeletal muscle.

10. The method as described in claim 1, further comprising the introduction of growth factors following the attaching of said skeletal muscles to said heart.

11. The method as described in claim 1, wherein said chronic pattern comprises delivering stimulus pulses synchronized to a first predetermined fraction of the patient's natural heartbeats, and said changed pattern comprises delivering stimulus pulses synchronized to a second predetermined fraction of the patient's natural heartbeats, where said second fraction is greater than said first fraction.

12. A method of treating a patient having angina by electrically stimulating collateral blood flow from a first portion of the patient's heart to a normally functioning portion of said patient's myocardium, comprising operatively connecting a portion of said patient's skeletal muscle to said first portion and to said normally functioning myocardial portion, and stimulating said skeletal muscle with a pattern of stimulus pulses so as to electrically induce said collateral blood flow from said first portion through said skeletal muscle to said normally functioning portion without substantial mechanical activation of the patient's heart.

* * * * *